(12) United States Patent  
Olsson et al.

(10) Patent No.: US 8,540,429 B1
(45) Date of Patent: Sep. 24, 2013

(54) SNAP-ON PIPE GUIDE

(75) Inventors: Mark S. Olsson, La Jolla, CA (US); Eric M. Chapman, Santee, CA (US); Allen W. Tucker, San Diego, CA (US); Dawn E. Shaffer, San Diego, CA (US)

(73) Assignee: SeeScan, Inc., San Diego, CA (US)

( * ) Notice: Subject to any disclaimer, the term of this patent is extended or adjusted under 35 U.S.C. 154(b) by 547 days.

(21) Appl. No.: 12/658,939

(22) Filed: Feb. 16, 2010

Related U.S. Application Data

(63) Continuation-in-part of application No. 12/371,540, filed on Feb. 13, 2009, now Pat. No. 8,289,385.

(51) Int. Cl.
*F16C 29/02* (2006.01)
*F16L 9/18* (2006.01)

(52) U.S. Cl.
USPC ............................................. 384/29; 138/112

(58) Field of Classification Search
USPC ...... 403/326, 335, 336, 338, 364; 15/104.05, 15/104.095; 285/305, 319, 81; 405/183.5, 405/184.4; 138/108, 110, 111–114, 148, 138/157–162
See application file for complete search history.

(56) References Cited

U.S. PATENT DOCUMENTS

| 1,646,463 | A | * | 10/1927 | Stokesberry | 285/409 |
| 6,862,945 | B2 | | 3/2005 | Chapman et al. | 73/865.8 |
| 2008/0136163 | A1 | * | 6/2008 | Okada | 285/2 |

* cited by examiner

*Primary Examiner* — Alan Waits
(74) *Attorney, Agent, or Firm* — Steven C. Tietsworth, Esq.

(57) ABSTRACT

A pipe guide includes a pair of cylindrical shells each having a plurality of radially extending circumferentially spaced vanes and structure for holding the shells together when the shells are axially mated end-to-end. A pair of curved tab arms extend circumferentially about corresponding ones of the cylindrical shells. A pair of slide-locks are configured to slide over corresponding ones of the tab arms to move them into a locking position in which keys on the tab arms extend between adjacent coils of a coil spring surrounded by the shells.

25 Claims, 10 Drawing Sheets

SNAP-ON PIPE GUIDE

CROSS-REFERENCE TO RELATED APPLICATION

This application is a continuation-in-part of co-pending U.S. patent application Ser. No. 12/371,540 filed Feb. 13, 2009, the entire disclosure of which is hereby incorporated by reference.

FIELD OF THE INVENTION

This invention relates to devices facilitating the guidance of push-cables and inspection cameras being moved through pipes, conduits or other hard-to-access areas.

BACKGROUND OF THE INVENTION

Long lengths of pipe already in place frequently require inspection for diagnosis or repair. Examples are sewage lines, gas and water lines and cable conduits. Pipes or conduits requiring inspection may often have small diameters of six inches or less, and may make sharp turns or have internal joining, for example, which make the progress of a pipe inspection camera through the pipe or conduit difficult. A pipe inspection camera head that is coupled to the distal end of a push-cable and that that is jammed a significant distance down a pipe can be difficult to un-lodge, adding time and cost to the inspection. Additionally, it is desirable to keep the camera head of a pipe inspection system raised above the bottom of the pipe to avoid fouling or obscuring it with sludge, water, or debris. To this end, pipe guides using various designs have been developed. See, for example, U.S. Pat. No. 6,862,945 granted Mar. 8, 2005 to Eric Chapman et al. Pipe guides in the existing art often are built of multiple parts requiring intricate assembly, and may be awkward or difficult to attach to an inspection system.

SUMMARY

In accordance with the present invention a pipe guide includes a pair of cylindrical shells each having a plurality of radially extending circumferentially spaced vanes and structure for holding the shells together when the shells are axially mated end-to-end. A pair of curved tab arms extend circumferentially about corresponding ones of the cylindrical shells. A pair of slide-locks are configured to slide over corresponding ones of the tab arms to move them into a locking position in which keys on the tab arms extend between adjacent coils of a coil spring surrounded by the shells.

DETAILED DESCRIPTION

The present invention provides a pipe guide that is more easily assembled, attached and removed around the spring that extends rearwardly from a camera head in a video pipe inspection system. In this type of system a termination assembly mechanically connects the fiberglass rod of a flexible resilient push-cable to the camera head and also electrically connects wires in the cable to the electronic circuitry inside the camera head. An elongate stainless steel coil spring surrounds the terminal segment of the push-cable. The forward end of the spring is connected to the rearward end of the camera head. The spring provides a means for matching the mechanical impedance of the rigid camera head to the push-cable. The spring absorbs the stresses of the shocks, bends and twists that might otherwise lead to breakage of the electrical connections.

Figure 1:
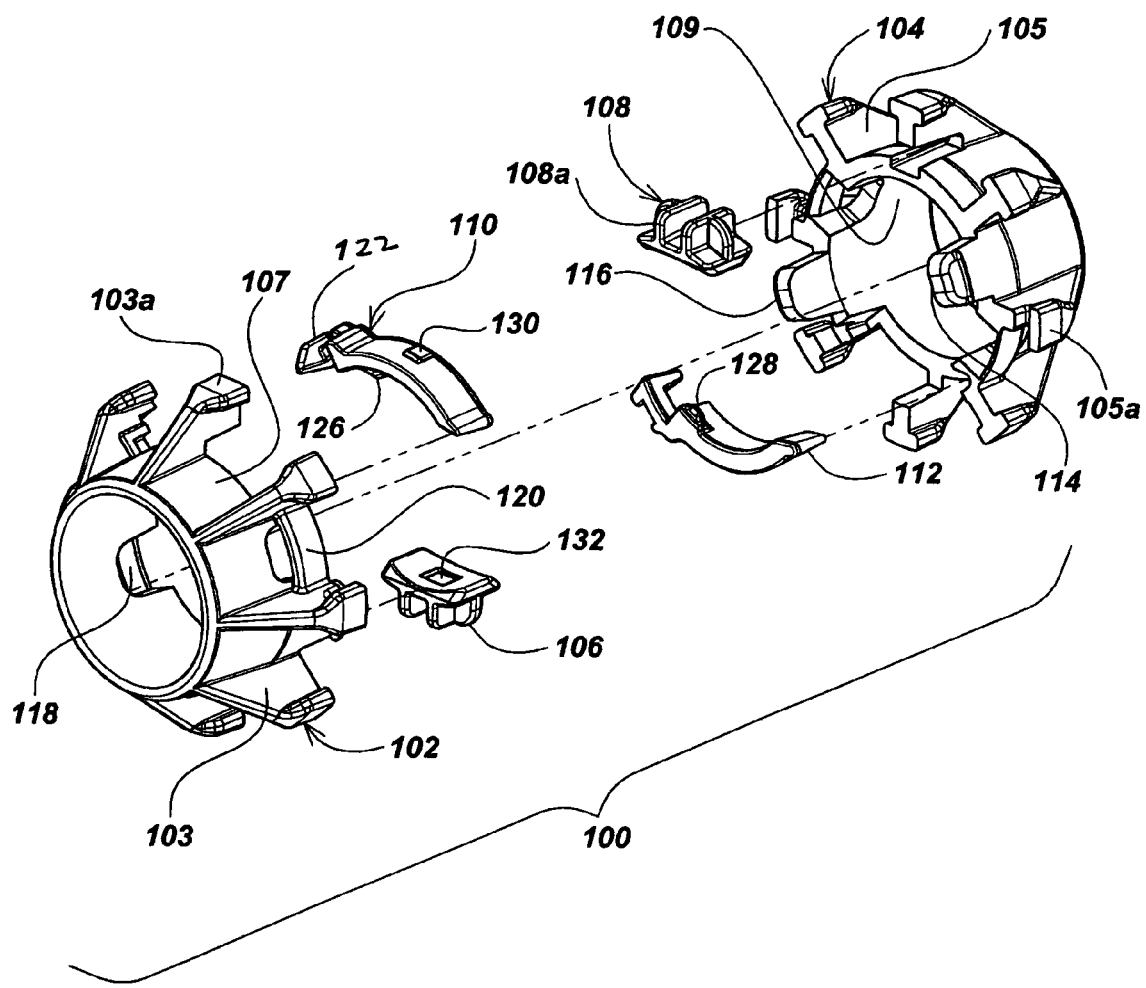
FIG. 1 is an exploded isometric view of a pipe guide in accordance with an embodiment of the present invention.

Referring to FIG. 1, in accordance with an embodiment of the present invention, a pipe guide 100 comprises two groups of three parts in each group. Each group forms a half of the pipe guide 100 and includes a cylindrical shell 102, 104 a tab arm 110, 112 and a slide-lock 106, 108. When assembled these parts form two mirror-image halves that can be readily snapped together around the spring 304 (FIG. 9) of a pipe inspection system. One half of the pipe guide 100 (FIG. 2) is turned to face the other and rotationally offset by one-eighth of a turn. The two halves then lock together to produce the assembled pipe guide 100 (FIG. 3). The components of the pipe guide 100 are preferably injection molded out of suitable plastic.

Each shell 102, 104 (FIG. 1) has eight substantially identical vanes 103, 105 that extend radially outwardly from its surface. These generally triangular vanes 103, 105 provide tapered frontal edges on the forward end of the pipe guide 100 that facilitate insertion of the camera head down the pipe. The vanes 103, 105 are advantageously formed with skids 103a and 105a on the outer ends thereof which have flat radial surfaces that engage the interior wall of the pipe and provide better stability and increased wear resistance. The vanes 103, 105 extend axially and are equally circumferentially spaced around the corresponding inner cylindrical portions 107, 109 of the shells 102, 104, respectively. Two lock tongues 114, 116 (FIG. 1) extend axially from the perimeters of each of the shells 102, 104. The shells 102, 104 also each have two formed catches 118, 120 (FIGS. 1 and 7) that provide recesses for receiving and engaging the lock tongues 114, 116 that extend from the opposite shell. Each of the catches 118, 120 is formed as a circumferentially° extending rib. The act of engaging the lock tongues 114, 116 into their opposite-side recesses under the catches 118, 120 locks the shells 102, 104 of the assembled pipe guide 100 together. Each of the lock tongues 114, 116 is configured to be received under the corresponding one of the catches 118, 120 when the shells 102, 104 are axially mated end-to-end. Each of the lock tongues, such as 114, has a radially outwardly projecting barb 114a (FIG. 2) formed on the outer end thereof. When the shells 102, 104 are mated the tongues 114, 116 deflect radially inwardly under their corresponding catches 118, 120 and once the barbs are axially past the catches 118, 120 they deflect radially outwardly and the barbs lock the shells 102, 104 together.

In each shell 102, 104, two of the vanes 103, 105 (FIG. 3) have recesses formed at their bases to receive the corresponding tab arms 110, 112 that are curved and extend circumferentially. Each tab arm 110, 112 is formed with a pair of parallel upstanding tabs such as 122 (FIG. 1) that slide over opposite sides of a corresponding vane. In each shell one of the vanes has a recess formed at its base for receiving a corresponding slide-lock 106, 108. The slide-locks 106, 108 each have a pair of parallel upstanding flanges such as 108a (FIG. 1) that slide over opposite sides of the corresponding vanes 103, 105.

The pipe guide 100 is rapidly assembled by dropping the tab arms 110, 112 into the correct recesses in the vanes, dropping the slide-locks 106, 108 into the corresponding recesses in the vanes, rotationally aligning the two shells 102, 104, and sliding them together until the locking tongues 114, 116 engage and snap-lock under their respective circumferentially extending catches 118, 120. The pipe guide 100 need only be assembled once, and can be repeatedly installed or removed thereafter using the tab arms 110, 112 and slide-locks 106, 108.

Figure 2:
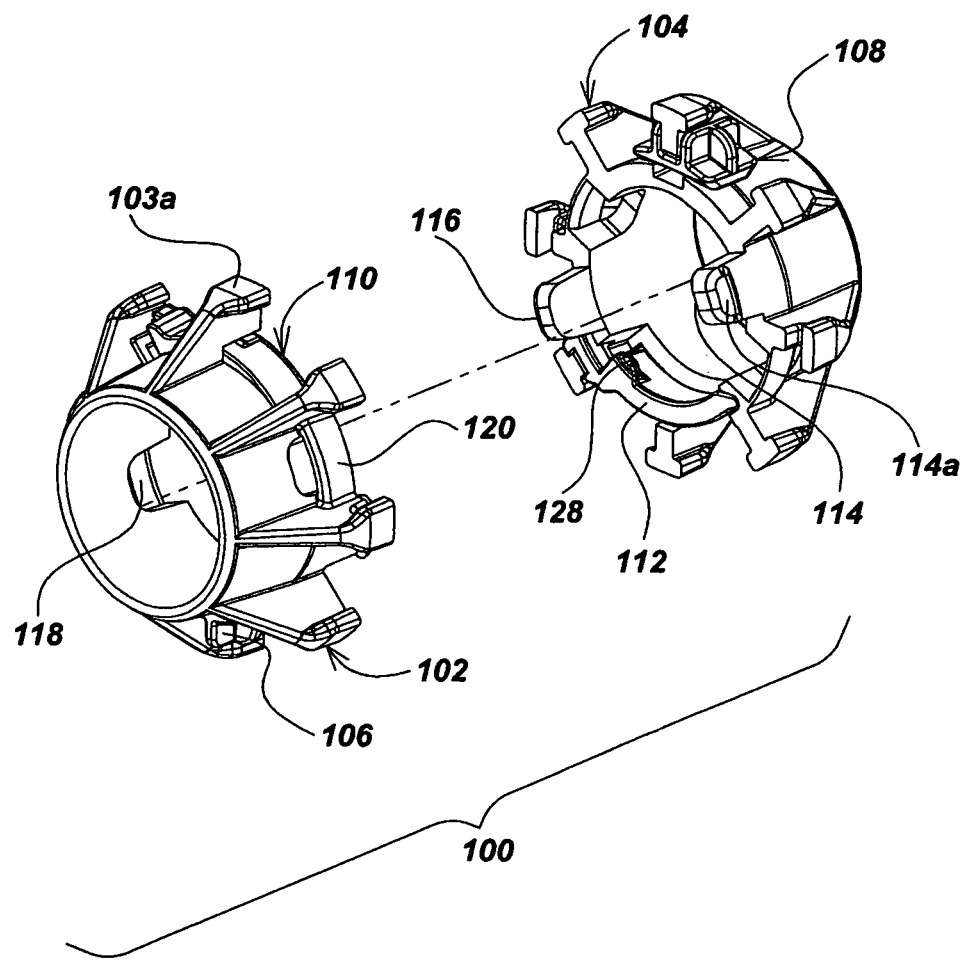
FIG. 2 is an exploded view of the components illustrated in FIG. 1 partially assembled into two mating halves.
Figure 3:
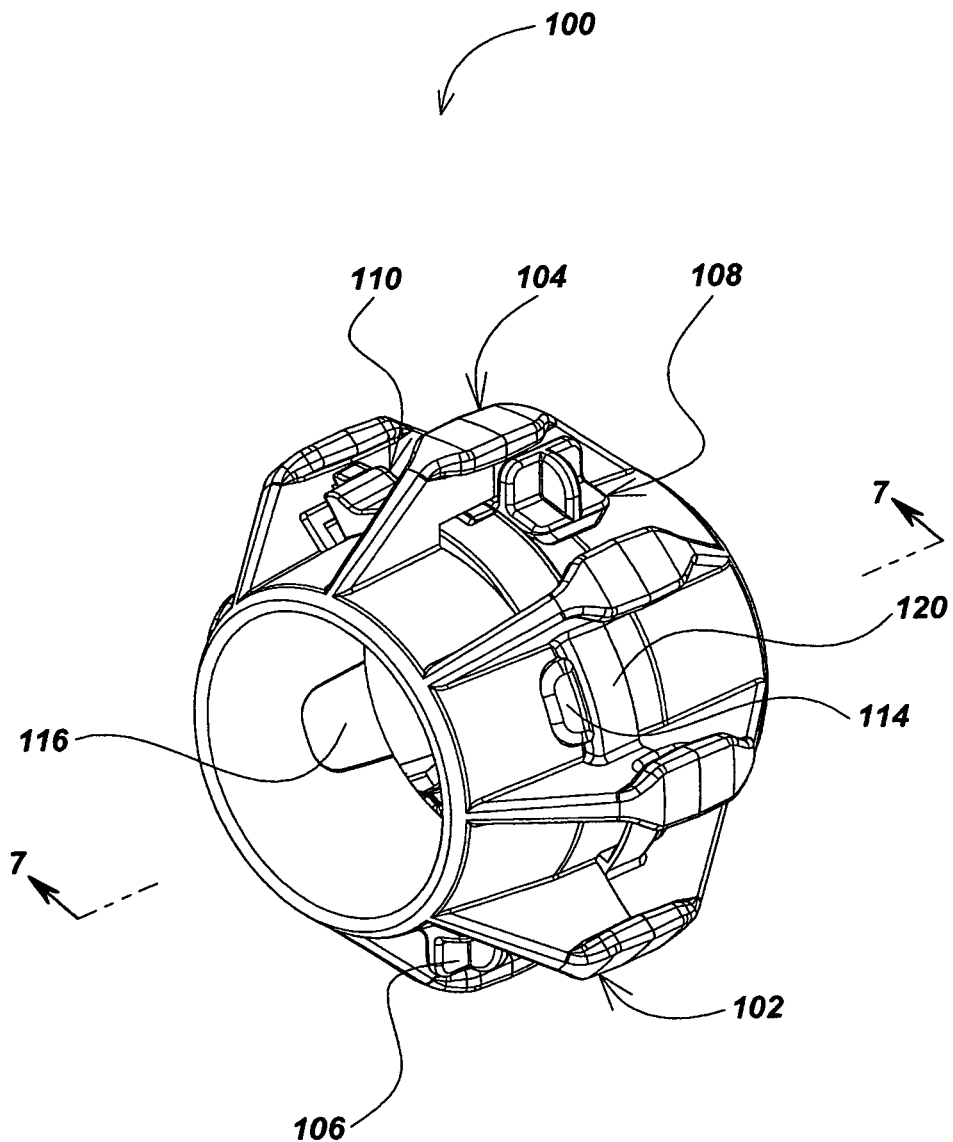
FIG. 3 is an enlarged isometric view of the assembled pipe guide of FIG. 1 in its unlocked configuration in which it may be slid into position around the spring of a pipe inspection system.

FIG. 2 illustrates the two halves with the tab arms 110, 112 and the slide-locks 106, 108, inserted into the recesses in their respective shells 102, 104, prior to locking the two halves together. The two locking tongues 114, 116 protrude from shell 104 aligned with matching catches 118, 120 in shell 102. The tongues on shell 102 are not visible in this view.

Figure 4:
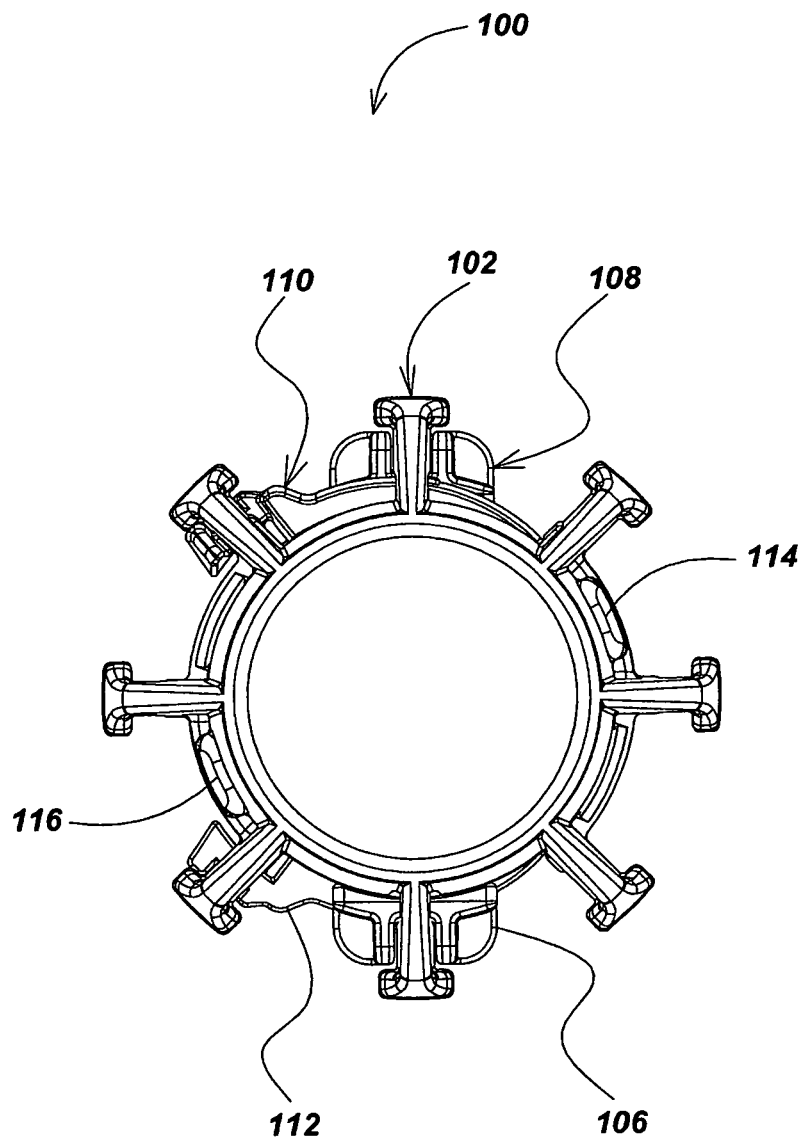
FIG. 4 is an end view of the assembled pipe guide taken from the left side of FIG. 3.

The tabs on the tab arms 110, 112 lie to either side of one vane when the tab arm is seated in its corresponding shell. When the tab arms 110, 112 are in their downward or locked positions, pressing tabs 122, 124 (FIG. 6) formed on the extreme ends of the tab arms 110, 112 toward the intermediary vane will force the tab arm to shift upward (unlock) provided the slide-locks 106, 108 are in unlocked, i.e. not overlapping the tab arms 110, 112. In FIGS. 3 and 4, this would be a clockwise force on tab arm 110, for example. When a tab arm is in its unlocked, upper position pressing the inner tab downward toward the central axis of the pipe guide 100 will force the tab arm to shift downward into its locking position. In FIG. 3 this would be a downward force on tab arm 110. The design of the tab arms 110, 112 causes these movements to occur with a positive click as the tab arm's wedge-shaped key passes up or down through its opening in the shell. The lower face of each tab arm 110, 112 has a small wedge-shaped key 126 and 128 (FIG. 6) formed into the same.

The slide-lock 108 in shell 104 is seated in a formed recess such that when the two shells 102, 104 are locked together, it will be able to slide axially over the flat surface of tab arm 110 if the tab arm is in its depressed position, thus locking the tab arm 110 into the depressed position. Slide-lock 106 can similarly slide axially over and lock down tab arm 112.

Figure 9:
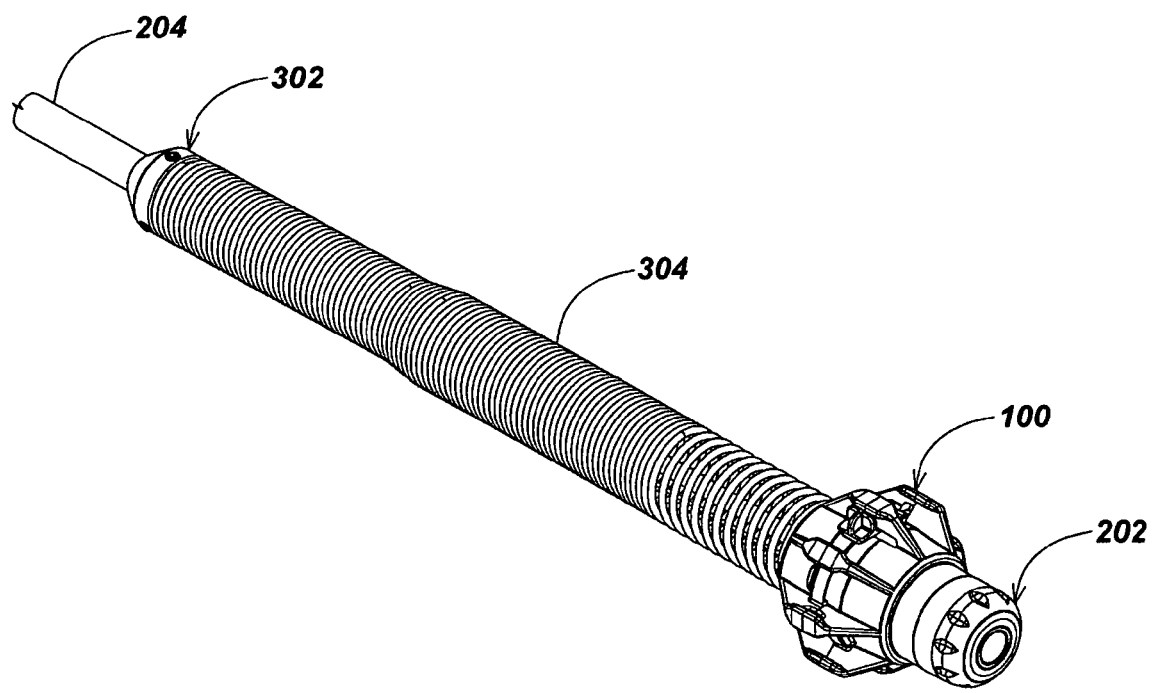
FIG. 9 is a reduced isometric view of the pipe guide of FIG. 1 locked in position around the spring of a pipe inspection system rearwardly of its camera head.

When a slide-lock 106, 108 is in position over a tab arm 110, 112, a small raised surface 130 (FIG. 1) on the tab arm 110 fits removably into a small indentation in the slide-lock, similar to indentation 132 on slide-lock 106. This alignment creates a friction interlock which holds slide-lock 108 onto tab arm 110, and slide-lock 106 onto tab arm 112. Thus the tab arms 110, 112 and slide-locks 106, 108 have cooperating projections and detents that snap together. When the assembled pipe guide 100 is in position on the spring of a pipe inspection system and the tab arm 110 is depressed, the formed key 126 of the tab arm 110 will axially lock the pipe guide 100 into position on the coil-spring 304 which supports the camera head 202 as illustrated in FIG. 9.

FIG. 3 illustrates the assembled pipe guide 100 with the two halves of shells 102, 104 mated and locked together. In this view the tab arm 110 is in the raised or open, unlocked position, allowing the pipe guide 100 to be slid into position at the end of the coil spring 304 just behind the camera head 202. When the pipe guide 100 is correctly positioned, the operator may lower the tab arms 110, 112 into their depressed, locked positions by pressing on the end tabs of tab arm 110, 112 until the keys 226 and 128 wedge between adjacent coils of the spring 304. Tab arm 110 is then locked down by sliding slide-lock 108 axially across it. The same process is done with tab arm 112 and slide-lock 106, locking the pipe guide 100 on both sides of the coil spring.

FIG. 4 illustrates an end view of the pipe guide 100 when in the unlocked or open condition. Tab arms 110, 112 can be seen to be slightly raised from the outer surface of the cylindrical portions 107, 109 and the inner wall of the pipe guide 100 is uninterrupted by any protuberance. In this configuration, the pipe guide 100 is able to readily slide into position over the coil spring 100. It can also be seen in FIG. 4 that in the open position the raised tab arms 110, 112 prevent the slide-locks 106, 108 from moving over them.

Figure 5:
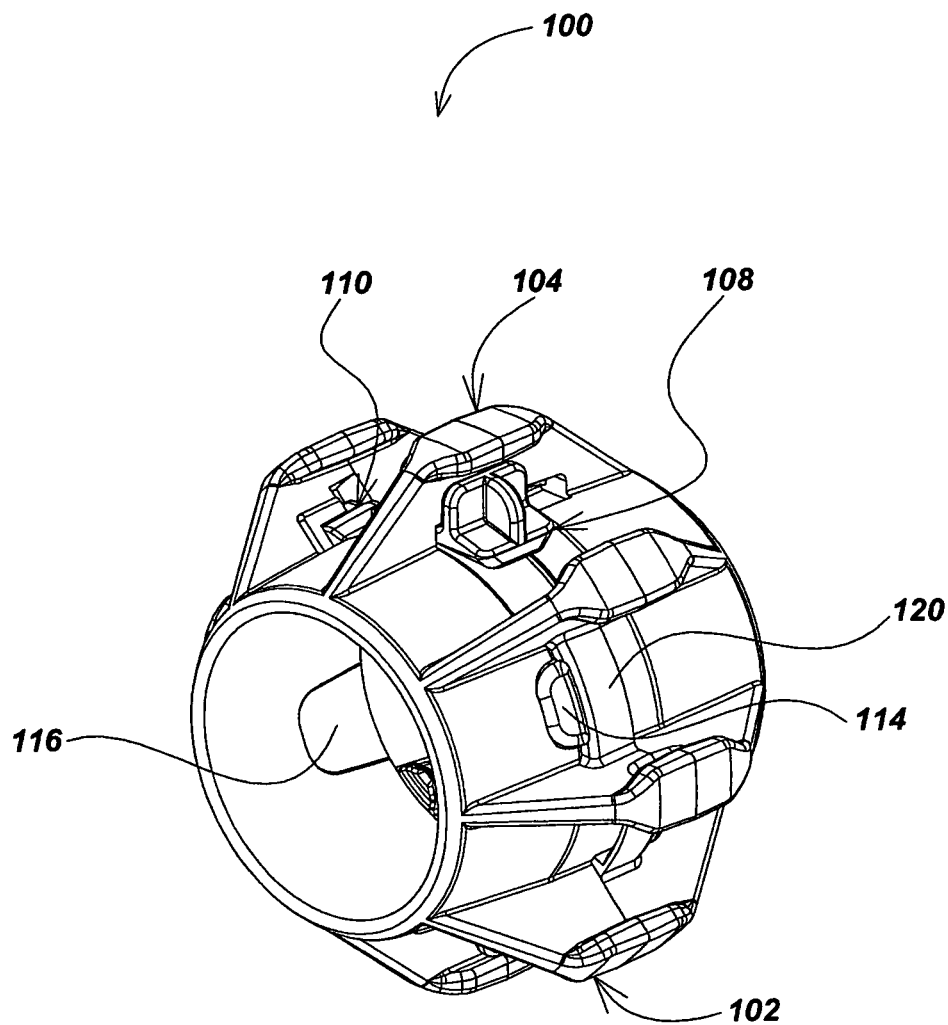
FIG. 5 is an isometric view of the assembled pipe guide of FIG. 1 in its locked configuration.

FIG. 5 is a perspective view of the pipe guide 100 with the tab arm 110 in its lowered or locking position. Slide lock 108 has been slid over the lowered tab arm 110 thus preventing it from working open in use. In this view the connection between the halves of the shell 102, 104 by reason of locking tongues 114 and 116 locking under the catches such as 120 can be clearly seen.

Figure 6:
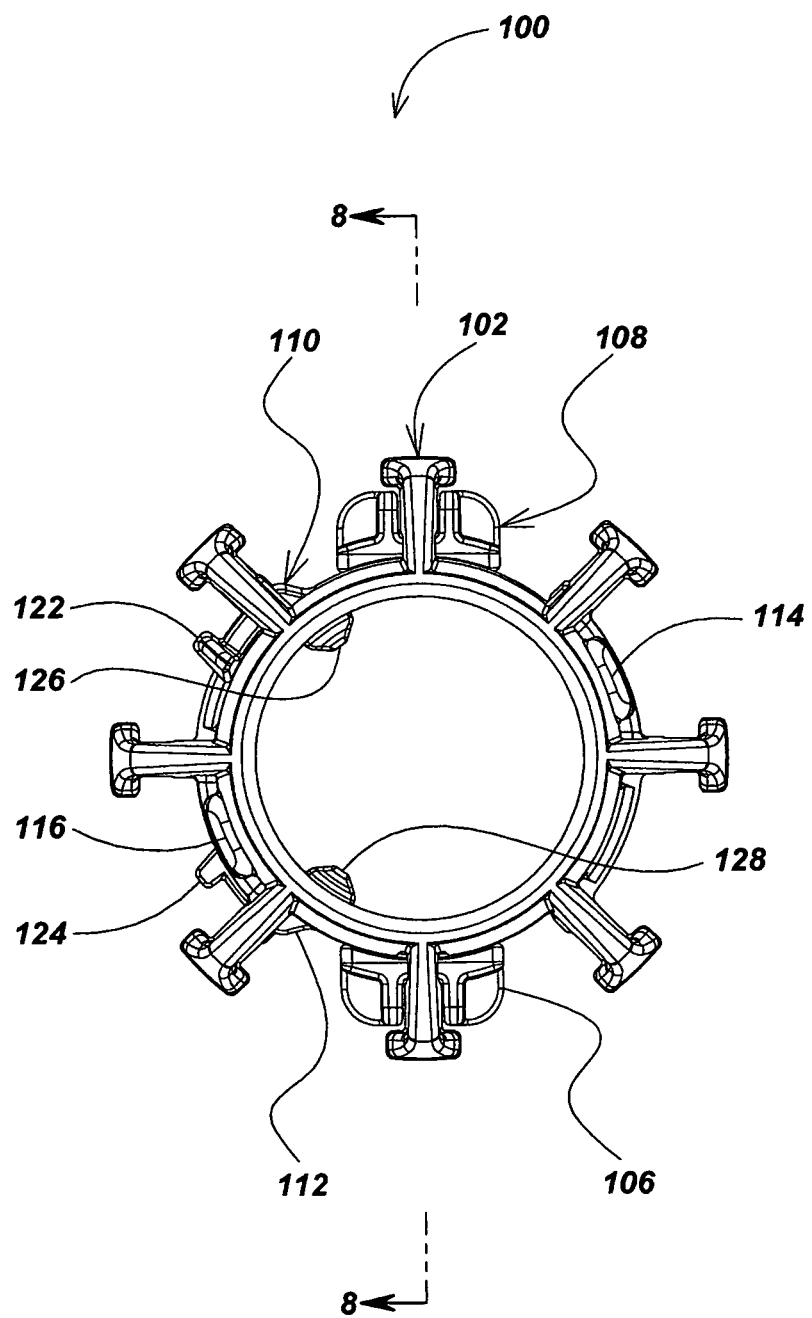
FIG. 6 is an end view similar to FIG. 4 illustrating the pipe guide in its locked configuration.

FIG. 6 is an end view of the pipe guide 100 when in its locked configuration. Here, the wedge-like keys 126, 128 formed in the undersides of tab arms 110 and 112 can be seen protruding inside the inner circumference of the pipe guide 100. Tab 122 on tab arm 110 and tab 124 on tab arm 112 have been pressed away from their respective dividing vanes causing the tab arms 110, 112 to shift downward and inserting the keys 126, 128 into the interior of the pipe guide. When the pipe guide 100 surrounds the coil spring 304 the keys 126, 128 are inserted between adjacent coils of the spring 304 to lock the pipe guide 100 longitudinally directly rearward of the camera head 202 in the proper position for supporting and guiding the same.

Figure 7:
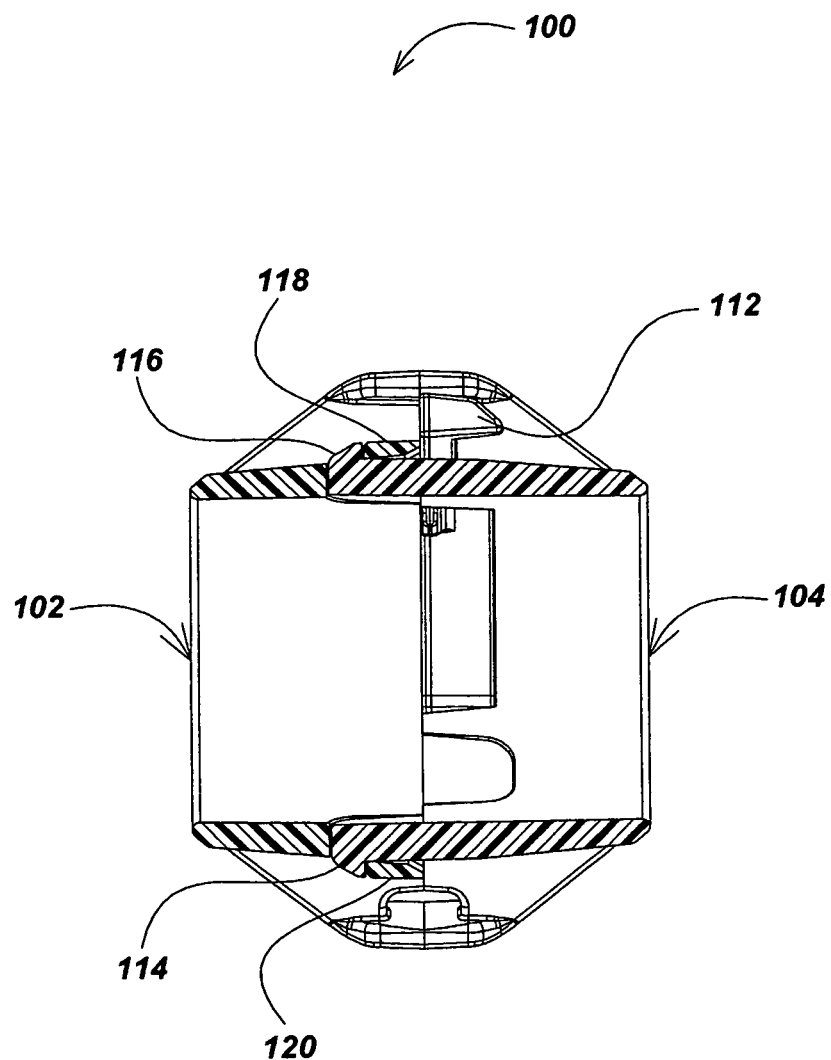
FIG. 7 is a sectional view of the assembled pipe guide taken along line 7-7 of FIG. 3.

FIG. 7 is a sectional view illustrating the locking action of tongues 114, 116 under the catches 118, 120. The curved forward edge of the tongue 114, 116 forces the edge of the catches 118, 120 upward until the projecting barbs on the leading edges of the tongues 114, 116 passes the raised edge, allowing it to snap down and lock the tongues 114, 116 in place. The locking of two tongues 114, 116 under their respective catches 118 120 on each shell 102, 104 holds the two halves of pipe guide 100 together.

Figure 8:
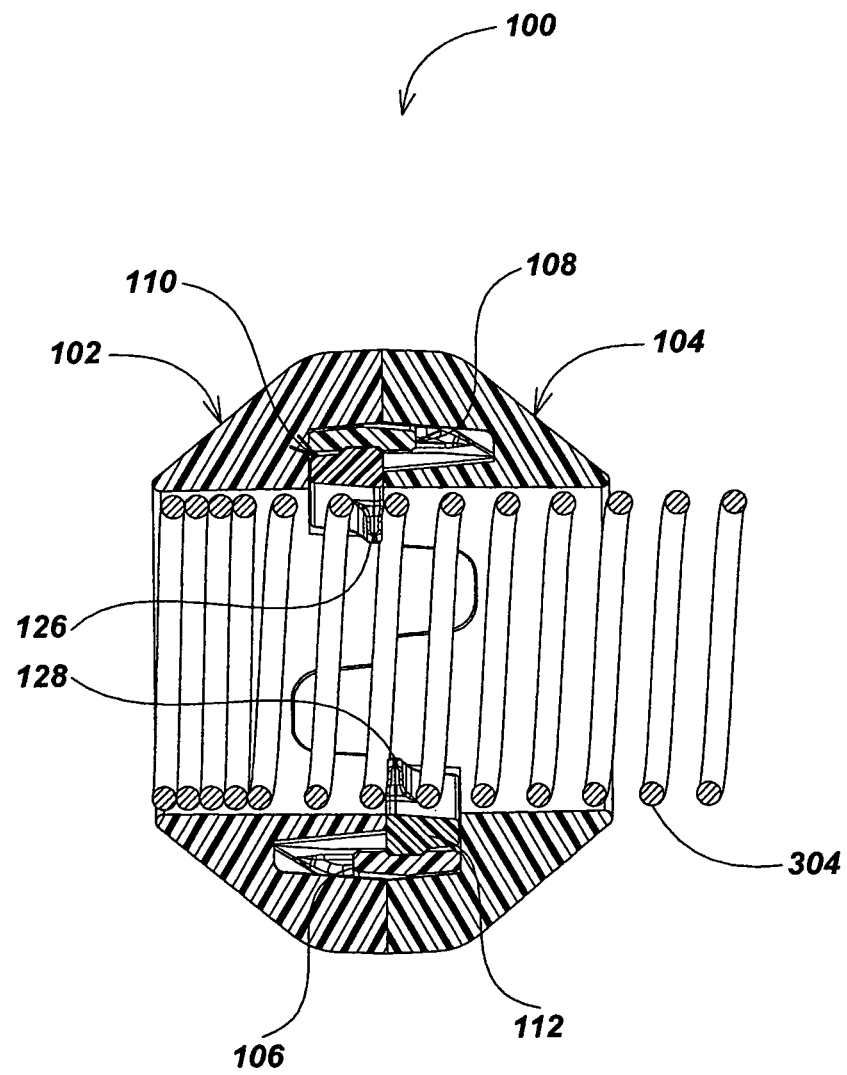
FIG. 8 is a sectional view taken along line 8-8 of FIG. 6 and illustrating the pipe guide locked into position around the coil spring of a pipe inspection system.

FIG. 8 is a cutaway view of pipe guide 100 locked into position around the coil spring 304. The wedge-shaped keys 126 and 128 are seen wedged between individual coils of the spring. Key 126 is an extension of tab arm 110 which is in turn locked into its depressed position by slide-lock 108. Key 128 is an extension of tab arm 112 which is in turn locked into its depressed position by slide-lock 106.

FIG. 9 illustrates the assembled pipe guide 100 in place and locked in position around the spring 304 of a typical video pipe inspection system. In FIG. 9, pipe guide 100 is seen placed immediately behind the camera head 202 at the distal end of the coil spring 304. The coil spring 304 is attached to a push-cable 204 by a termination adapter 302. Each of the tab arms 110, 112 in pipe guide 100 is locked in its depressed or locked position, causing the associated keys 126, 128 to wedge between the spring coils below, thus firmly fixing the pipe guide 100 in position.

Figure 10:
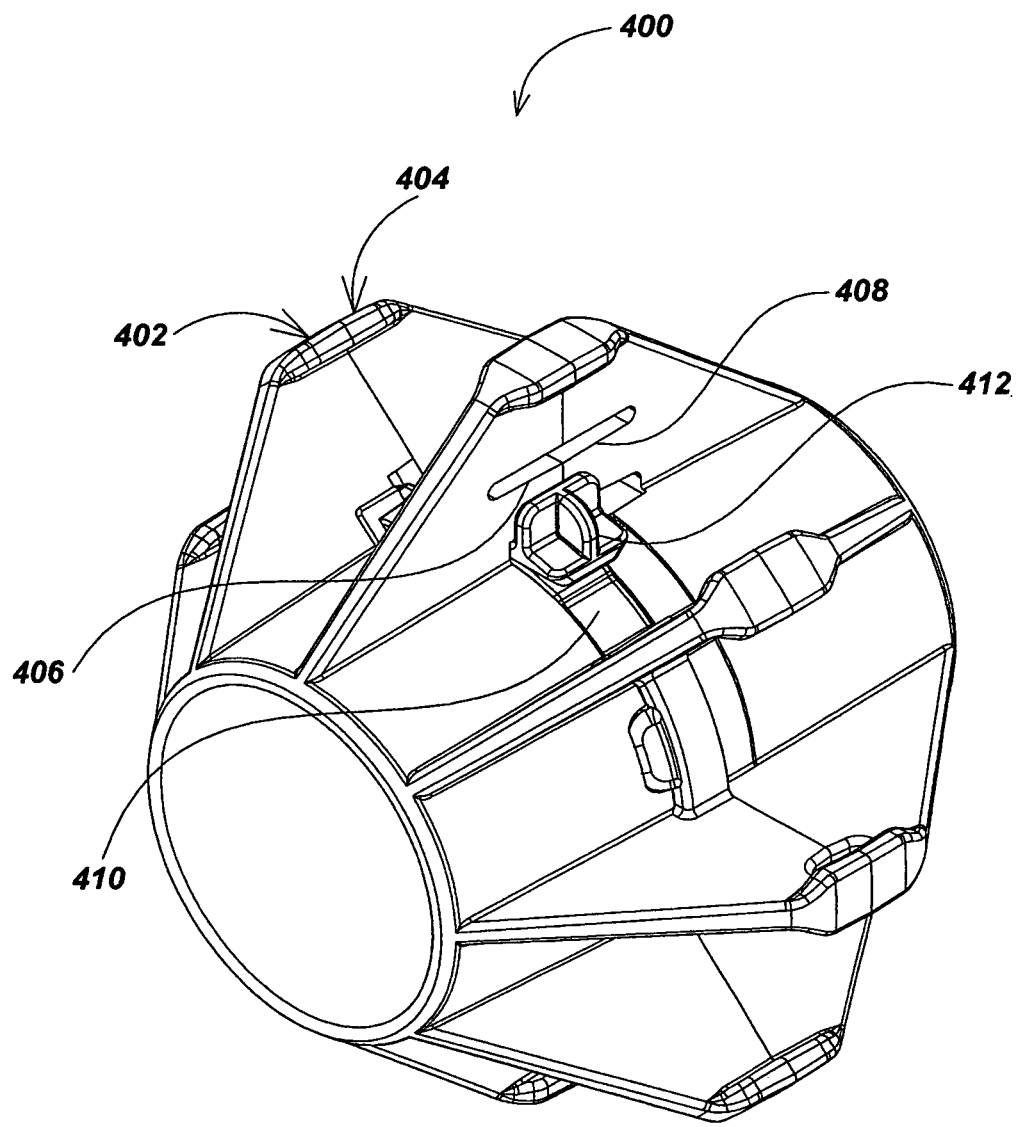
FIG. 10 is an enlarged isometric view of an alternate embodiment of the pipe guide of the present invention that incorporates an alternative vane design.

An alternate embodiment of the present invention is illustrated in FIG. 10. In assembly 400, the two shell halves 402, 404 each have a slot 406, 408 formed in the vane above each slide-lock recess. When assembled the two slots form a single slot above the slide-lock 412 parallel to the channel in which the slide-lock 412 moves when it is slid into locking position over the locked tab arm 410. The presence of the slots 406, 408 provides a degree of spring-like flexure in the portion of the vane below the slot which enables the slide-lock 412 to be pressed downward when it is in position over the tab arm 410. This flexure also provides a positive locking force to reinforce the locking action of the slide-lock 412 and prevent accidental displacement of the slide-lock.

Clearly, other adaptations and modifications of the present invention will occur to those skilled in the art in view of the teachings set forth above. The pipe guide may be scaled to a larger diameter for larger video pipe inspection systems. More locking tabs may be designed into a larger version, and the precise form of the shells used to form the pipe guide may be adapted for other systems as needed. The vanes could be replaced with other forms of pipe centering and stand-off means such as flexible brush bristles, spokes and cuffs. Therefore, the protection afforded the present invention should only be limited by the following claims, which include all such embodiments and modifications when viewed in conjunction with the above specification and accompanying drawings.

We claim:

1. A pipe guide, comprising:
    a pair of cylindrical shells, each shell having a plurality of radially extending circumferentially spaced vanes and each shell having a structure for holding the shells together when the shells are axially mated end-to-end;
    a curved tab arms extending circumferentially about each of the cylindrical shells; and
    a pair of slide-locks configured to slide over corresponding ones of the tab arms to move the tab arms into a locking position in which keys on the tab arms extend between adjacent coils of a coil spring surrounded by the shells.

2. The pipe guide of claim 1 wherein each of the slide-locks are deflected radially inwardly as the slide-locks are slid axially over their corresponding tab arm.

3. The pipe guide of claim 1 wherein the vanes each have tapered frontal edges.

4. The pipe guide of claim 1 wherein at least one vane on each shell has a first recess for receiving one of said tab arms.

5. The pipe guide of claim 1 wherein the vanes have skids on their outer ends for engaging an interior wall of a pipe.

6. The pipe guide of claim 1 wherein the tab arms and slide-locks have corresponding cooperating projections and detents that couple together with a snapping action.

7. The pipe guide of claim 1 wherein the keys are wedge-shaped.

8. The pipe guide of claim 1 wherein the keys extend radially through corresponding openings in the shells.

9. The pipe guide of claim 1 wherein each tab arm has a pair of upstanding tabs that slide on opposite sides of a corresponding vane of a shell.

10. The pipe guide of claim 1 wherein the slide-locks each have a pair of parallel upstanding flanges that slide over opposite sides of a corresponding vane of a shell.

11. The guide of claim 1, wherein each of the cylindrical shells includes:
    a lock tongue; and
    a catch for receiving the lock tongue of the other of the pair of shells to lock the shells together.

12. The guide of claim 11, wherein the lock tongue includes an outwardly projecting barb to secure the lock tongue to a corresponding catch on the other of the pair of shells.

13. The guide of claim 1, wherein the slide locks include one or more upstanding flanges for sliding over one or more sides of a vane.

14. The guide of claim 1, wherein the tab arms include one or more tabs to lock or unlock.

15. A pipe guide, comprising:
    a pair of cylindrical shells each having a plurality of radially extending circumferentially spaced vanes, at least one axially extending lock tongue, and at least one circumferentially extending catch, each of the lock tongues being configured to be received by the corresponding one of the catches as the shells are axially mated end-to-end;
    a pair of curved tab arms that are received in a first set of recesses formed in corresponding ones of the vanes and extend circumferentially relative to the cylindrical shells; and
    a pair of slide-locks that are received in a second set of recesses formed in corresponding ones of the vanes wherein the pair of slide-locks are configured to slide over corresponding ones of the tab arms to move the tab arms into a locking position in which keys on the tabs extend between adjacent coils of a coil spring surrounded by the shells.

16. The pipe guide of claim 15 wherein each of the slide-locks are deflected radially inwardly as the slide-locks are slid axially over their corresponding tab arms.

17. The pipe guide of claim 15 wherein the vanes each have tapered frontal edges.

18. The pipe guide of claim 15 wherein the vanes adjacent the second set of recesses have slots formed therein.

19. The pipe guide of claim 15 wherein the vanes have skids on their outer ends for engaging an interior wall of a pipe.

20. The pipe guide of claim 15 wherein the tab arms and slide-locks have cooperating projections and detents that snap together.

21. The pipe guide of claim 15 wherein the keys extend radially through corresponding openings in the shells.

22. The pipe guide of claim 15 wherein the slide-locks each have a pair of parallel upstanding flanges that slide over opposite sides of a corresponding vane of a shell.

23. The pipe guide of claim 15 wherein each tab arm is formed with a pair of parallel upstanding tabs that slide over opposite sides of a corresponding vane of a shell.

24. A guide, comprising:
    a pair of cylindrical shells, each shell having a tongue and a catch to secure a tongue of the other cylindrical shell;
    a plurality of vanes extending radially from each of the shells;
    at least one curved slide arm mounted on each of the shells and having a interior-facing key portion that is movable radially inwardly to a locked position to anchor each of the shells to a coil spring; and
    a circumferentially movable slide lock to slide over the curved slide arm in a first direction to position the key portion of the curved slide arm in said locked position and slide over the slide arm in a second direction opposite the first direction to release the shells from the coil spring.

25. The guide of claim 24, wherein the key portion comprises a wedge-shaped key.

* * * * *